United States Patent [19]

Morris et al.

[11] 4,061,736

[45] * Dec. 6, 1977

[54] PHARMACEUTICALLY ACCEPTABLE INTRAMOLECULARLY CROSS-LINKED, STROMAL-FREE HEMOGLOBIN

[75] Inventors: Kent C. Morris, Mountain View; Pieter Bonsen, Los Altos, both of Calif.; Myron B. Laver, Weston, Mass.

[73] Assignee: Alza Corporation, Palo Alto, Calif.

[*] Notice: The portion of the term of this patent subsequent to Jan. 4, 1994, has been disclaimed.

[21] Appl. No.: 727,066

[22] Filed: Sept. 27, 1976

Related U.S. Application Data

[63] Continuation-in-part of Ser. No. 553,514, Feb. 2, 1975, Pat. No. 4,001,401, and a continuation-in-part of Ser. No. 554,051, Feb. 2, 1975, Pat. No. 4,001,200.

[51] Int. Cl.² .................. A61K 37/02; C12B 3/00; C07G 7/00

[52] U.S. Cl. .................................... 424/177; 195/1.7; 260/112 B; 260/112.5 R; 424/101

[58] Field of Search ................. 424/101, 177; 195/1.7; 260/112.5 R, 112 B

[56] References Cited

U.S. PATENT DOCUMENTS

| | | | |
|---|---|---|---|
| 4,001,200 | 1/1977 | Bonsen et al. | 260/112.5 R |
| 4,001,401 | 1/1977 | Bonsen et al. | 424/177 |

*Primary Examiner*—Sam Rosen
*Attorney, Agent, or Firm*—Paul L. Sabatine; Thomas E. Ciotti; Edward L. Mandell

[57] ABSTRACT

This invention concerns pharmaceutically acceptable intramolecularly cross-linked, stromal-free hemoglobin. The intramolecularly cross-linked, stromal-free hemoglobin is useful as a blood substitute for carrying oxygen to tissues and vital organs, as a blood plasma expander, and for supplying oxygen to oxygen-requiring environments.

22 Claims, 8 Drawing Figures

PHARMACEUTICALLY ACCEPTABLE INTRAMOLECULARLY CROSS-LINKED, STROMAL-FREE HEMOGLOBIN

CROSS REFERENCE TO RELATED APPLICATIONS

This application is a continuation-in-part of U.S. patent application Ser. No. 553,514 filed on Feb. 2, 1975, now U.S. Pat. No. 4,001,401 and U.S. patent application Ser. No. 554,051, filed on Feb. 2, 1975, now U.S. Pat. No. 4,001,200. This application and the related applications are assigned to the same assignee, and benefit of their filing dates is claimed herein.

BACKGROUND OF THE INVENTION

1. Field of the Invention

The present invention relates to novel and useful (1) intramolecularly cross-linked, stromal-free deoxyhemoglobin, and (2) intramolecularly cross-linked, stromal-free oxyhemoglobin. The intramolecularly cross-linked stromal free hemoglobins of this invention have the property of reversibly binding gaseous ligands such as oxygen, and they are useful as blood substitutes for transporting and supplying oxygen to vital tissues and organs, as blood plasma substitutes as sources of oxygen for biological systems, and for furnishing oxygen to oxygen-consuming environments.

2. Description of the Prior Art

Hemoglobin is present in the blood of mammals and it has the fundamental property in solution of reversible oxygenation. In its natural form, mammalian hemoglobin is a conjugated, non-crosslinked protein having a molecular weight of 64,500 and structurally comprised of two pairs of sub-units. Each sub-unit contains a heme group and a polypeptide chain, called globin. In mammals, hemoglobin is present in erythrocytes along with stroma which consists of proteins, phospholipids and cholesterol. *Clinical Hematology*, by Wintrobe, 6th Ed., pages 138 to 199, 1967, published by Lea and Febiger, Philadelphia, Pa. The reaction of isolated, bovine hemoglobin containing stroma with glutaraldehyde is known to the art in *Histochemical J.*, Vol. 2, pages 137 to 150, 1970, wherein Hopwood used an excess of glutaraldehyde to obtain an insoluble precipitate. Similarly, the reaction of whole blood proteins with glutaraldehyde leading to a water insoluble glue is disclosed by Karjala, et al, in the U.S. Pat. No. 3,294,564. The interaction of the collagen and collagen degradation product gelatin with diisocyanates and other polycoupling agents, including aldehydes, is reported by Campbell in U.S. Pat. No. 2,591,133, by Linder, et al, in U.S. Pat. No. 3,057,782, and by Bowes in *Biochimica et Biophysica Acta*, Vol. 168, pages 341 to 352, 1968. The carboxyalkylation of globin for use as a plasma expander is taught by Biddison in U.S. Pat. No. 2,719,837; however, the products obtained by the above reactions lacked the ability to transport oxygen and in consequence thereof, they did not enter into general use. In U.S. Pat. No. 2,527,210, Bower disclosed the use of hemoglobin for treating wounds, in U.S. Pat. Nos. 3,000,836 and 3,519,572, Ginsburg and Kita disclosed blood preparations having utility as standards for measuring hemoglobin. In *Federation Proceedings*, Vol. 34, pages 1458 to 1460, 1975, Mok et al. disclosed the reaction of hemoglobin solutions containing stromal-free protein with diimidate esters leading to intramolecularly cross-linked and intermolecular complexes. In U.S. Pat. No. 3,925,344, Mazur disclosed a plasma protein substitute consisting of intramolecularly cross-linked hemoglobin formed by using diimidate cross-linking agents. In these latter two references, the reaction was carried out apparently in an air environment and free of reducing conditions which leads to hemoglobin in the oxygenated form. A diimidated cross-linked hemoglobin similar to the product of U.S. Pat. No. 3,925,344 also is disclosed in Netherland Pat. No. 7,041,140.

OBJECTS OF THE INVENTION

It is an immediate object of this invention to provide both intramolecularly cross-linked, stromal-free deoxyhemoglobin and oxyhemoglobin useful as blood substitutes and blood plasma expanders possessing enhanced physical and chemical integrity in the environment of use.

Still a further object of the invention is to provide both intramolecularly cross-linked, stromal-free deoxyhemoglobin and oxyhemoglobin useful as blood substitutes and blood plasma expanders and having increased intravascular persistence over a prolonged period of time.

Yet a further object of the invention is to provide new and useful therapeutic agents useful as blood substitutes and blood plasma expanders that are miscible with blood and its components, and are substantially non-toxic, non-antigenic and non-pyrogenic.

Yet still a further object of the invention is to provide novel blood substitutes and blood plasma expanders that are readily available, stable under prolonged storage and are safely discharged from circulation.

Still another object of the invention is to provide blood substitutes that can transport and supply oxygen to vital tissues and organs.

Yet still a further object of the invention is to make available both intramolecularly cross-linked, stromal-free deoxyhemoglobin and oxyhemoglobin solutions having an osmolality substantially equal to whole blood with utility as a volume replenisher.

Yet still another object of the invention is to make available to the art both intramolecularly cross-linked, stromal-free deoxyhemoglobin and intramolecularly cross-linked, stromal-free oxyhemoglobin possessing colloid and oncotic properties useful for maintaining the level of blood and plasma in the management of disease.

Still a further object of the invention is to make available new compositions of matter, comprising both intramolecularly cross-linked stromal-free deoxyhemoglobin and oxyhemoglobin that can take over certain functions of plasma and have the oxygen carrying function of red blood cells.

Still a further purpose of the invention is to provide new biologically active molecules of defined and homogenous molecular weight that are soluble in physiological fluids and can be used as a blood substitute and blood plasma expander without an accompanying risk of transmission of disease.

These objects as well as other objects, features and advantages of this invention, will become more readily apparent to those skilled in the art from the following detailed description, the drawings and the accompanying claims.

SUMMARY OF THE INVENTION

This invention concerns both an intramolecularly cross-linked, stromal-free deoxyhemoglobin, and an intramolecularly cross-linked, stromal-free oxyhemoglobin. By deoxyhemoglobin is meant a stromal-free tetramer of the formula deoxyHb$_4$, and by oxyhemoglobin is meant a stromal-free tetramer of the formula oxyHb$_4$. By intramolecularly cross-linked is meant the covalent cross-linking of sub-units within the respective tetramers.

The products of the invention are prepared from a member selected from the group consisting of stromal-free mammalian deoxyhemoglobin and oxyhemoglobin, which in either instance, are intramolecularly cross-linked with a bifunctional or a polyfunctional cross-linking agent. The products are soluble in aqueous fluids having a pH of 6 to 9, in physiological fluids including blood and plasma, and in pharmaceutically acceptable carriers such as crystalloid, electrolyte, carbohydrate, colloid, and polymeric solutions. The products have a molecular weight of approximately 64,500 and they have the property in solution of reversibly binding gaseous ligands in an amount up to 60 $\mu$ mol of ligan per gram of intramolecularly cross-linked, stromal-free deoxyhemoglobin and intramolecularly cross-linked, stromal-free oxyhemoglobin, that is, for both products the oxygen-carrying capacity is close to 100%. The products, depending on their preparation exhibit a partial oxygen pressure at half-saturation of 2.5 mm Hg to 120 mm Hg at 37° C, measured at neutral pH and atmospheric pressure. The products have acceptable colloid osmotic properties, the ability to react reversibly with oxygen, that is to transport and deliver oxygen, and a prolonged plasma survival time in vivo as seen by a half-life of more than 2 to 3 times that of free hemoglobin, usually about 180 to 240 minutes measured in rats. The products also can be used for the storage and preservation of viable isolated perfused mammalian organs, such as those of humans, household pets, sport and valuable farm animals for their eventual transplant into a recipient, and as a priming fluid in extracorporeal circulatory assist devices.

DETAILED DESCRIPTION OF PREPARATION OF PRODUCTS OF THE INVENTION

Figure 1:
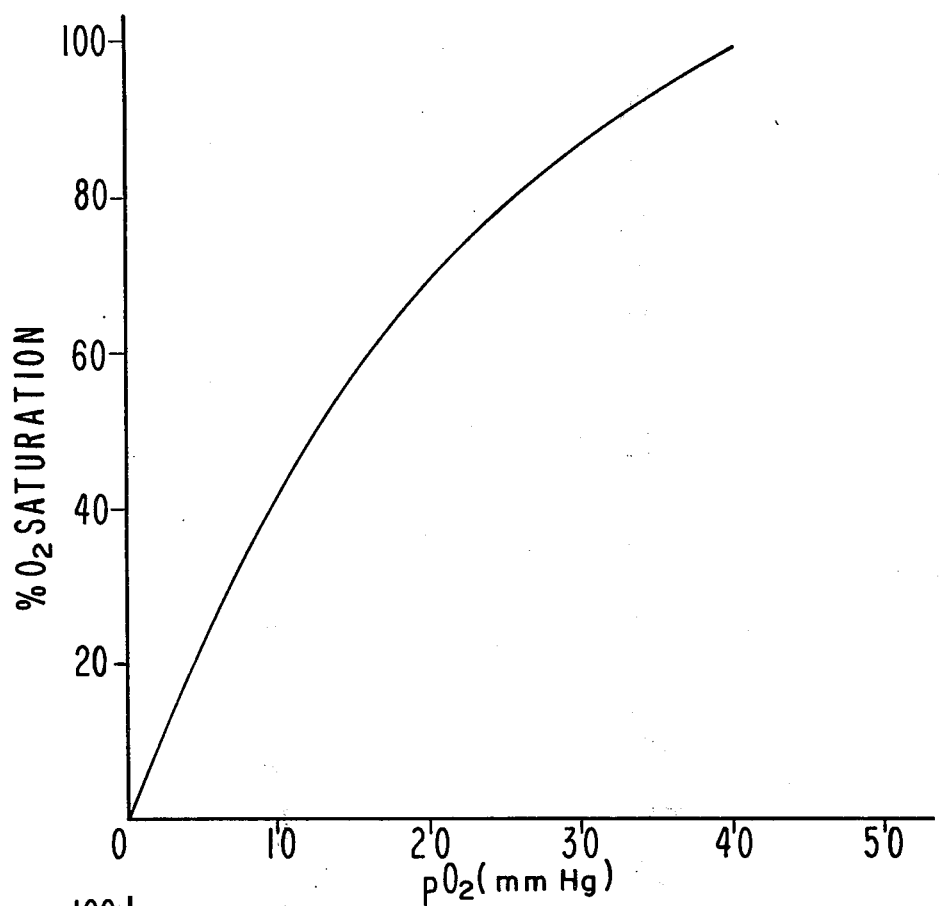

The products of the invention, intramolecularly cross-linked, stromal-free deoxyhemoglobin and intramolecularly cross-linked, stromal-free oxyhemoglobin are prepared by starting with erythocytes separated from freshly drawn human blood, from outdated whole blood, placentas or packed erythrocytes obtained from human donor centers, or from erythrocytes obtained from animal blood. The blood is drawn into bottles containing an anticoagulant, centrifuged, and the supernatant plasma withdrawn. Centrifuging is carried out at $-5°$ C to 40° C, preferably at 4° C to 6° C, for about 5 to 60 minutes, and at 650 to 6500g, with the supernatant plasma and buffy coat removed and discarded. Next, the red cells are washed in about 1 to 4 volumes of cold, isotonic saline, or hypertonic sodium chloride, the suspension centrifuged and the supernatant removed and discarded. The red cells are washed an additional 2 to 3 times, with the wash discarded after each centrifugation.

The method of obtaining the starting material for the cross-linking includes isolating hemoglobin from cells substantially free of cellular debris and stroma. The removal of stromal proteins and lipids is critical to the invention as its removal essentially eliminates renal damage as known to the prior art where hemoglobin solutions containing these were used as blood substitutes. The general procedure used herein for obtaining stromal-free hemoglobin includes first lysing the cells in about one to four volumes of cold water or other lysing solutions such as hypotonic phosphate buffers, or hypotonic saline. After lysing, the red cell suspension is shaken and cold toluene is added in about 10 to 200% of the cell volume, usually about 10 to 30% of the volume. The mixture is then shaken for 4 to 10 minutes and left standing at 4° C to 6° C for 24 to 72 hours to produce a triphasic mixture. The lower, clear red layer is isolated and centrifuged at 40,000 to 50,000g for at least 60 minutes at about 4° C to 6° C. Then, the upper clear supernatant is separated and filtered through a diatomaceous earth filter. This filtration removes any traces of stroma, and various precipitation tests can be used to ascertain if the hemoglobin is stromal-free. Suitable tests are described in Hawk's *Physiological Chemistry*, pages 181 to 183, 1965, published by McGraw-Hill Company. Similar methods for obtaining stromal-free hemoglobin are reported in *Journal of Experimental Medicine*, Vol. 126, pages 185 to 193, 1969; *Annals of Surgery*, Vol. 171, pages 615 to 622, 1970; *Haematologia*, Vol. 7, pages 339 to 346, 1973; and *Surgery*, Vol. 74, pages 198 to 203, 1973.

Residual low molecular weight salts and metabolites are removed from the stromal-free hemoglobin by dialysis against standard or medically acceptable buffers. Buffers suitable for the purpose include 0.05 M phosphate and physiological saline buffered with alkali bicarbonates. The stromal-free hemoglobin is dialyzed by using commercially available equipment such as a Dow miniplant using Biofiber ®- 50 dialysis fiber, the Kolff system using a semipermeable membrane or a Crom-A-Coil ® unit dialyzer. Semipermeable dialysis membranes operable for the purpose include cellulose, cellulose acetate, modified cellulose acetate membranes such as N,N-diethylamino ethylcellulose acetate and cellulose propionate.

The dialysis is carried out at 4° C and 6° C by passing stromal-free hemoglobin solution through hollow cellulosic fibers, with the hemoglobin dialized against a buffer passed along the outside of the fiber. Generally, the fibers have an exclusion limit that permits passage of low molecular weight solutes without egress of hemoglobin. The flow rate of the fluid is greater than 1 ml per minute, preferably 3 to 25 ml per minute. The stromal-free hemoglobin is passed through the fibers three times to establish equilibrium. Suitable dialysis methods are reported in *Methods of Enzymology*, Vol. XXII, pages 23 to 32, 1971, published by Academic Press, New York.

Next, the dialyzed hemoglobin is intramolecularly cross-linked to form water soluble intramolecularly cross-linked, stromal-free hemoglobin. The stromal-free hemoglobin for cross-linking can be either liganded, that is oxyhemoglobin, or unliganded, that is deoxyhemoglobin, corresponding to the presence or the absence of a heme ligand. When oxygen is present as the heme ligand, the hemoglobin is known as oxyhemoglobin. When there is no heme ligand present, the hemoglobin is deoxyhemoglobin. These hemoglobins are described in Hawk's *Physiological Chemistry*, pages 335 to 342, 928 to 940, and 1090 to 1099, published in 1965 by McGraw-Hill Book Company. The oxyhemoglobin is prepared by equilibration with oxygen, at a temperature of 4° to 6° C, for about 30 minutes to 60 minutes. Deoxyhemoglobin is prepared by repeated evacuation of the solution under decreased pressure, usually about 250 mm Hg, followed by flushing with nitrogen or an inert gas such as argon or neon. Deoxyhemoglobin can also be prepared by chemical deoxygenation with the addition of reducing agents such as sodium dithionite, or sodium sulfite. The presently preferred forms of hemoglobin for intramolecularly cross-linking with a cross-linking agent that produces soluble products are oxyhemoglobin and deoxyhemoglobin. As it has now been found, intramolecular cross-linking of these hemoglobins produces (1) intramolecularly cross-linked, stromal-free deoxyhemoglobin of molecular weight about 64,500, having a $P_{50}$ value of from about 4 mm to about 100 mm Hg at physiological conditions, 37° C and at a pH of 7.1 to 7.3, depending on the method of preparation of the product; and (2) intramolecularly cross-linked, stromal-free oxyhemoglobin of molecular weight 64,500 having a $P_{50}$ value of 2.5 mm to 25 mm Hg at physiological conditions as stated above. These $P_{50}$ values include the hemoglobin oxygen affinities as found in blood and free, naturally occurring hemoglobin.

The intramolecular cross-linking of dialyzed stromal-free hemoglobin is carried out by the intramolecular cross-linking of usually the primary amino groups of its lysine residues to yield water-soluble products. The cross-linking is performed in the presence of at least one bi- or polyfunctional covalent cross-linking agent to produce the desired intramolecularly cross-linked, stromal-free product. The cross-linking is carried out by first purging the reaction vessel with the appropriate gaseous ligand, such as oxygen for the synthesis of intramolecularly cross-linked, stromal-free oxyhemoglobin; and with an inert gas such as nitrogen, or argon, for the synthesis of intramolecularly cross-linked, stromal-free, deoxyhemoglobin. Then, the hemoglobin is cross-linked under a blanket of the appropriate gas, that is oxygen, argon, or nitrogen. The reaction is performed at a temperature of 0° to 25° C, from 1/4 hours to 300 hours, and at normal atmospheric pressure. Elevated pressures up to 5 atmospheres can also be used. Generally, about 1 equivalent of reactant hemoglobin, tetramer, having a molecular weight of 64,500, is reacted with 1 mol to 150 mols of the bi- or polyfunctional cross-linking reagent.

It is essential to the invention that the cross-linking agent used yield intramolecularly cross-linked hemoglobin soluble in aqueous and physiological media. This is achieved by using the agents and reaction conditions described below. The stromal-free hemoglobin and cross-linking reagents are thoroughly mixed and allowed to react with constant stirring for about ¼ hours to 300 hours at 4° to 6° C. The reaction is terminated by quenching with from 5 to 250 equivalents of a low molecular weight amine, or an excess thereof. High level thermal oxidation of hemoglobin is prevented by carrying out the reaction at low temperatures, usually 0° C to 10° C. Any increase in reaction temperature is accompanied by shorter reaction times. As the concentration of the cross-linking reactants are increased, the tendency for intermolecular cross-linked products to form can increase, and this is prevented by decreasing the reaction time or by the addition of a low molecular weight amine, or a mixture of low molecular weight amines. The amount of amine added is an amount sufficient to react with the unreacted functional group of a cross-linking agent bound to a hemoglobin moiety, usually a stoichometric amount or an excess up to 250 equivalents of amine to one equivalent of cross-linking agent. Following addition of the quenching amine, the reaction is stirred an additional 18 to 24 hours at 4° C. The crude reaction mixture is clarified by centrifugation and dialyzed against an isotonic electrolyte solution. The soluble product obtained is sterilized by filtering through a filter having a pore size of about 0.20 to 0.45 microns, preferably 0.22 microns.

The bi- or polyfunctional cross-linking agents suitable for the purpose of the invention are preferably stable to hydrolysis yet reactive with cross-linkable sites of the hemoglobin tetramer to yield an intramolecularly cross-linked water soluble product. The cross-linking agents used do not adversely effect hemoglobin, its solubility, or its function of reversibly binding oxygen for supplying it to tissues and organs. The bi- or polyfunctional cross-linking agents have at least two functional groups, and they can be the same or different. These groups are capable of reacting with and intramolecularly cross-linking amino groups and other cross-linkable sites on the heomgolbin tetramer. By amino groups is meant the N-terminal alpha amino group of the hemoglobin chains, and those of the basic amino acid residues such as lysine and arginine.

The functional groups of the cross-linking agent can be covalently bonded to each other or they can be separated by an aliphatic or by an aromatic ring. Exemplary aromatic stabilized functional groups are azo and halo activated with a nitro group. These include compounds having a heterocyclic ring with reactive groups bonded to the ring. For example, triazines of the formula:

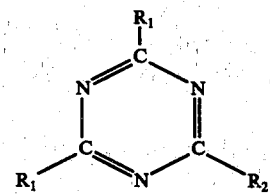

wherein $R_1$ is halogen including fluoro, chloro and bromo, and $R_2$ is a nucleophilic substituent such as an aliphatic or aromatic group, a halogen, a lower alkyl of 1 to 8 carbons, and amino. Cross-linking agents embraced by this formula are 2-amino-4,6-dichloro-s-triazine and chloro-s-triazine. The cross-linking agents include aromatic stablized agents prepared by the diazotation of an aromatic diamine, for example, benzidine and its derivatives with nitrous acid to yield bis-diazobenzidines of the formula:

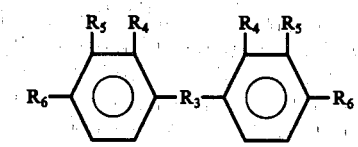

wherein $R_3$ is a member selected from the group consisting of a covalent bond, alkylene of 1 to 5 carbons, phenylene, ether, sulfone and secamine, $R_4$ is halogen or nitro, $R_5$ is hydrogen, nitro, lower alkyl of 1 to 8 carbons, sulfonate ($SO_3H$) and carboxylate, and $R_6$ is halogen, diazo (—N:N—), isocyanate (NCO), and isothiocyanate (NCS). Representative agents embraced by the formula include bis-diazobenzidine 2,2'-sulfonic acid, 4,4'-difluoro-3,3'-dinitrophenylsulfone and diphenyl-4,4'-diisothiocyanate.

Cross-linking agents suitable for the invention include compounds of the formula:

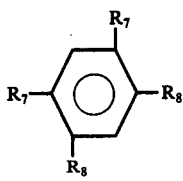

wherein $R_7$ is halogen and $R_8$ is nitro, or hydrogen with at least one $R_8$ a nitro, as represented by the commercially available activated halogenated reagent 1,5-difluoro-2,4-dinitrobenzene.

Cross-linking agents suitable for the purpose of the invention also include compounds of the formula $(R_9)_2C=0$ wherein $R_9$ is hydrogen or halogen, and compounds of the formula $R_{10}-(CH_2)_n-R_{10}$ wherein $R_{10}$ is the same or different and $n$ is 1 to 8. The agents also include compounds having a functional group bound to an aromatic moiety either directly or through an alkylene bridge of the formula $R_{10}-(CH_2)_m-C_6H_4-(CH_2)_m-R_{10}$ wherein $R_{10}$ is the same or different and $m$ is 0 to 3. Cross-linking agents include the compounds having the functional groups bonded to a cycloalkyl as represented by the formula:

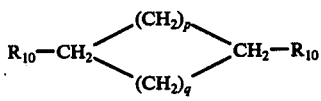

wherein $R_{10}$ is the same or different, $p$ is 0 to 4, and $q$ is 1 to 4. The cross-linking agents include compounds having functional groups bonded to an aliphatic chain interrupted with a nonfunctional group or having nonfunctional groups bonded to the chain as represented by compounds of the formula $R_{10}-(CH_2)_x-R_{11}-(CH_2)_x-R_{10}$ wherein $R_{10}$ is the same or different, $R_{11}$ is selected from the group consisting of an ether bridge, a divalent amine and a sulfone, and $x$ is an alkylene of 1 to 5 carbon atoms, with each $x$ the same or different. Representative of the functional group embraced by $R_{10}$ include isocyanate, vinyl, imine, isothiocyanate, isocyanide, aldehyde, epoxide, chloroformate, thiochloroformate, and imido lower alkyl ester, and thiolactones of the formula:

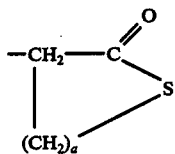

wherein $a$ is 1 to 3. Also, $R_{10}$ can be an activated group formed by reacting the carboxylic acid with a thionyl halide or phosphorus halide, or an activated group formed by reacting an amide or an alkyl ester of the carboxylic acid with hydrazine and then with nitrous acid to yield the corresponding activated group $COR_{12}$ wherein $R_{12}$ is halogen or azide. The activated group can also be formed by reacting the carboxylic acid with N,N'-carbonyl diimidazole or a carbodiimide of the formula $R_{13}-N=C=N-R_{13}$ wherein $R_{13}$ is the same or different and are a lower alkyl, a lower cycloalkyl, di(lower) alkyl amino lower alkylene, and heterocyclic lower alkyl including morpholino ethyl. $R_{12}$ can also be a

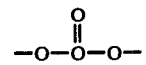

lower alkyl, and a

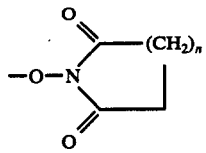

wherein $n$ is 1 or 2.

Exemplary commercially available cross-linking reagents embraced by the above formula include divinyl sulfone, epichlorohydrin, butadiene diepoxide, ethylene glycol diglycidyl ether, glycerol diglycidyl ether, un-syn-alkyl vinyl sulfone, propylene glycol diglycidyl ether, and propenyl sulfone.

Representative of compounds bearing a functional isocyanate or isothiocyanate group are the compounds listed below. Additionally, the isocyanates or isothiocyanates can be synthesized by reacting an alkyl or aryl amine with phosgene or thiophosgene. The isocyanates used for intramolecularly cross-linking are diisocyanates and they react with the free amino groups of stromal-free hemoglobin producing urea or thiourea cross-linked sites. Typical compounds include diphenyl-4,4'-diisothiocyanate-2,2'-disulfonic acid, toluene diisocyanate, toluene-2-isocyanate-4-isothiocyanate, 3-methoxydiphenylmethane-4,4'diisocyanate, propylene diisocyanate, butylene diisocyanate, and hexamethylene diisocyanate.

Exemplary of intramolecular cross-linking agents having an aldehyde or dialdehyde functionality include formaldehyde, paraformaldehyde, formaldehyde activated ureas such as 1,3-bis(hydroxymethyl)urea, N,N'-di(hydroxymethyl) imidazolidinone prepared from formaldehyde condensation with a urea according to the formula $CH_2O+R_{16}HN-CO-NHR_{16}\rightarrow HOCH_2NR_{1-6}-CH_2OH$ wherein $R_{16}$ is hydrogen, alkyl, aryl or heterocyclic ring. Other dialdehyde cross-linking agents include dialdehydes of the formula $OCH-R_{17}-HCO$ wherein $R_{17}$ is a member selected from the group consisting of a covalent bond and a straight or branched chain alkylene of 1 to 8 carbons. Dialdehydes embraced by the formula include gloxal, malonic dialdehyde, succinic dialdehyde, glutaraldehyde, adipaldehyde, 3-methyl glutaraldehyde, propyladipaldehyde, phthalic dialdehyde, terephthaldehyde and malonic dialdehyde.

Other intramolecular cross-linking agents include derivatives of carboxylic acids and carboxylic acid residues of hemoglobin activated in situ to give a reactive derivative of hemoglobin that will cross-link with the amines of another hemolgobin. Typical carboxylic acids useful for this purpose have the formula $CO_2H(CH_2)_n-CO_2H$, and $\{(CH_2)_nCOOH\}_3CH$ wherein $n$ is 1 to 8. The carboxylic acids include citric, malonic, adipic and succinic. Carboxylic acid activators include thionyl chloride, carbodiimides, N-ethyl-5-phenyl-isoxazolium-3'-sulphonate (Woodward's reagent K), N,N'-carbonyldiimidazole, N-t-butyl-5-methylisoxazolium perchlorate (Woodward's reagent L), 1-ethyl-3-dimethyl aminopropylcarbodiimide, 1-cyclohexyl-3-(2-morpholinoethyl) carbodiimide metho-p-toluene sulfonate. The cross-linking reaction using a carboxylic acid can be represented by the equation $RCO_2H \xrightarrow{activator} RCOX \xrightarrow{Hb-NH_2} RCONH-Hb$.

Other cross-linking groups that can be used are prepared from esters and thioesters activated by strained thiolactones, hydroxysuccinimide esters, halogenated carboxylic acid esters and imidates. The above functional reagents or methods for preparing them are reported in *Bull. Soc. Chem. Fr.*, Vol. 12, pages 4613 to 4617, 1971; *Biochemical Aspects of Reactions on Solid Supports*, by Stark, George R., Chapter 1, published by Academic Press, 1971; *Chemtech*, pages 47 to 55, 1974; *Rev. Pure and Appl. Chem.*, Vol. 21, pages 83 to 113, 1971; and British Pat. No. 1,252,770.

The cross-linking reagent can be a dialdehyde precursor that readily forms a bifunctional dialdehyde in the reaction medium. Suitable dialdehyde precursors include acrolein dimer or 3,4-dihydro-1,2-pyran-2-carboxaldehyde which undergoes ring cleavage in an aqueous environment to give alpha-hydroxy-adipaldehyde. Other precursors, which on hydrolysis yield a cross-linking reagent, include 2-ethoxy-3,4-dihydro-1,2-pyran which gives glutaraldehyde, 2-ethoxy-4-methyl-3,4-dihydro-1,2-pyran which yields 3-methyl glutaraldehyde, 2,5-diethoxy tetrahydrofuran which yields succinic dialdehyde and 1,1,3,3-tetraethoxypropane which yields malonic dialdehyde and formaldehyde from trioxane. The above bifunctional reagents are known in *Beilstein's Handbook*, Vol. 7, Suppl. 1, page 12; ibid, Vol. 1, Suppl. 2, page 12; ibid, Vol. 1, Suppl. 2, page 831; ibid, Vol. 1, Suppl. 3, page 3076; ibid, Vol. 1, Suppl. 2, page 824; and ibid, Vol. 1, Suppl. 2, page 572. Similarly, the cross-linking reagents can be prepared by known synthetic procedures such as malonaldehyde from tetraethyl acetal, succinaldehyde from diethoxytetrahydrofuran, and adipaldehyde by the oxidation of cyclohexanediol.

In the above formula, the expression "an alkylene of 1 to 8 carbons" includes straight or branched chain alkylenes such as methylene, ethylene, propylene, isopropylene and hexylene. The expression "lower alkyl of 1 to 8 carbons" includes straight or branched chain alkyls such as methyl, ethyl, propyl, isopropyl, and hexyl.

The low molecular weight amine added to the cross-linking vessel for regulating the cross-linking reaction, or for quenching it, is a mono-, di-, or multifunctional agent, preferably a primary amine of the formula $R-NH_2$. The amine should be water soluble to assist in maintaining the solubility characteristics of the cross-linked hemoglobin. Typical low molecular weight amines used to deactivate excess cross-linking agents are glycine, lysine, serine, threonine, alanine, ethanolamine, 2-aminoadipic acid and glutathione. Other compounds capable of deactivating the cross-linking agents are terminators such as bisulfites and diols capable of deactivating aldehydes, low molecular weight alcohols for deactivating activated carboxylic acids, activated halides and isocyanates, and sulfhydryls for deactivating epoxides and vinyls.

The following examples are set forth as representative methods that illustrate the spirit of the invention. These examples are not to be construed as limiting the scope of this invention as other equivalent means will be readily apparent to those skilled in the art in the light of the disclosure, the figures and the claims.

DESCRIPTION OF INVENTIVE EMBODIMENTS

EXAMPLE I

Preparation of stromal-free hemoglobin solution: The starting material was 5 units of out-dated human blood that contained anti-coagulant acid-citrate-dextrose solution. The blood was obtained from a local blood bank. First the blood was poured from the blood bank bags into autoclaved 500 ml centrifuge tubes. The tubes were capped and the blood, comprised of erythrocytes, leucocytes, platelets, and plasma was centrifuged at 5,000 rpm (4000g) for 30 minutes at 4° C. Then, the plasma and buffy coat containing the leucocytes and platelets were removed by suction through a sterile pipette and discarded. The sedimented erythrocytes which remained were washed four times by suspending in approximately three times their volume in ice-cold sterile 0.9% physiological saline or 1.6% sodium chloride solution. Following each wash, the cells were resedimented by centrifugation and the supernatent removed and discarded.

Next, the washed red cells were lysed with either an equal volume of ice-cold water or hypertonic, 0.05 M phosphate buffer, pH 7.2, to rupture the intact cell wall and free the hemoglobin. Lysis was completed by vigorously shaking the cellular water suspension for 1 to 2 minutes at room temperature. Then, the lysed cells were placed in a sterile 2 liter separatory funnel, the total volume of the solution was approximately 1,500 ml. The lysed erythrocyte-water mixture was freed of stroma by extraction with 350 ml of ice-cold reagent-grad toluene. Extraction was carried out by shaking in the funnel for at least 5 minutes.

After setting overnight at 4° C, the extraction mixture separates into three layers: an upper layer of toluene containing stroma and lipids; a middle layer of cellular debris; and a lower layer of dark red aqueous hemoglobin solution. The lower hemoglobin layer, 800 to 1200 ml, was separated and centrifuged at 19,000 rpm (50,000g) for 60 minutes at 4° C to sediment and remaining cell debris. If, after the toluene extraction, no separation of the layers occurs, the toluene-water cellular emulsion was broken by either centrifugation at 5,000 rpm (4,000g) for 30 minutes at 4° C, or by treating the emulsion with 0.15 volumes of Celite ®-535 filtrant, a diatomaceous earth filter. The aqueous hemoglobin solution was removed from the Celite ® by vacuum filtration and centrifuging at 19,000 rpm (50,000g). Any last trace of stroma in the hemoglobin was removed by either filtering through filters of pore size 0.22 μ or by passage through a 1½ inch layer of wet-packed Celite ®-535 filtrant, that was previously acid-washed, then washed with sterile pyrogen-free water.

Next, the freshly prepared stromal-free hemoglobin solution was dialyzed against 0.05 M phosphate buffer, pH 7.6 using a Dow Biofiber ®-50 miniplant dialyzer. The hollow semipermeable cellulosic fibers of the dialyzer were first washed with 2.5% formalin and then rinsed with sterile pyrogen-free water to prevent possible bacterial contamination of the hemoglobin. The outside of the dialysis hollow fibers was flushed with sterile water and sterile phosphate buffer. Then, the hemoglobin solution was passed through the fibers at a flow rate of 20 ml per minute while the buffer was passed around the outside of the fibers, the buffer flowed in the opposite direction of the hemoglobin at a rate of 100 ml per minute. The hemoglobin solution was repeatedly passed through the fibers, at least three times, to insure complete electrolyte exchange and removal of cellular potassium ion. The hemoglobin solution was further clarified and made sterile by pressure filtration through a 0.22 μ filter comprised of mixed esters of cellulose, commercially available from Millipore Corporation. The stromal-free hemoglobin solution was analyzed to determine if it was stromal-free by adding about 1 ml of ice-cold saturated ammonium sulfate dropwise to 1 ml of hemoglobin solution with constant stirring. The absence of a precipitate indicated a stromal-free solution. The hemoglobin solution was stored at 4° to 6° C until needed.

Cross-linking of hemoglobin in oxyhemoglobin and deoxyhemoglobin conformation was carried out in like manner except that the atmosphere of the reaction vessel was made to correspond to the form of hemoglobin present. The cross-linking of deoxyhemoglobin was performed with oxygen-free solvents, prepared by boiling the solvent under an inert gas and stored under an inert atmosphere. The cross-linking described in the examples below are not intended to limit the invention as these and other equivalents will be apparent in the light of the present examples.

EXAMPLE II

Intramolecular cross-linking of stromal-free deoxyhemoglobin with hexamethylene diisocyanate: a 70 ml solution of stromal-free oxyhemoglobin, 11.3% w/v in 0.05 M phosphate buffer, pH 6.9, at 4°–6° C, was deoxygenated by equilibration with nitrogen. The pH of the anaerobic solution was adjusted to 7.4 by the addition of 1 ml of 1 N NaOH. The cross-linking agent, hexamethylene diisocyanate, 0.25 ml, was dissolved in 35 ml of toluene previously degassed by evacuation and reequilibration with nitrogen gas. The bifunctional cross-linking agent, in toluene, was added to the deoxyhemoglobin solution and the two phases intimately mixed. The molar reaction ratio, $Hb_4$lysine, assuming 44 lysine amino acid residues for each hemoglobin tetramer, to hexamethylene diisocyanate, was approximately 2.7 to 1. The emulsion was left standing at 4°–6° C under nitrogen overnight.

Next, the emulsion was oxygenated with 100% $O_2$ gas and broken by centrifugation at low speed, 4000g. Any residual toluene present was removed from the intramolecularly cross-linked, stromal-free deoxyhemoglobin solution by careful extraction with pentane. Next, 7.5 ml of 1.3 ml L-lysine in 0.05 M phosphate buffer, pH 7.2, was added to deactivate any unreacted isocyanate groups. The solution was left stirring at 4° C under air overnight. The reaction solution is clarified by centrifuging and filtering through a 0.65 micron filter. The clarified solution is dialyzed against an appropriate electrolyte solution to remove unbound cross-linking agent and excess lysine.

Optionally, cations and other components can be added to the solution at this step of the procedure. Also, the pH can be adjusted to the pH of the environment of use and the solution can be sterilized by filtering through an autoclaved filteration unit holding a filter with a pore size of about 0.22μ. In accompanying FIG. 1, the oxygen dissociation curve for intramolecularly cross-linked, stromal-free deoxyhemoglobin cross-linked with hexamethylene diisocyanate according to this example is set forth. The curve shows a $P_{50}$ value of 12.5 mm Hg at 37° C and neutral pH.

EXAMPLE III

Figure 2:
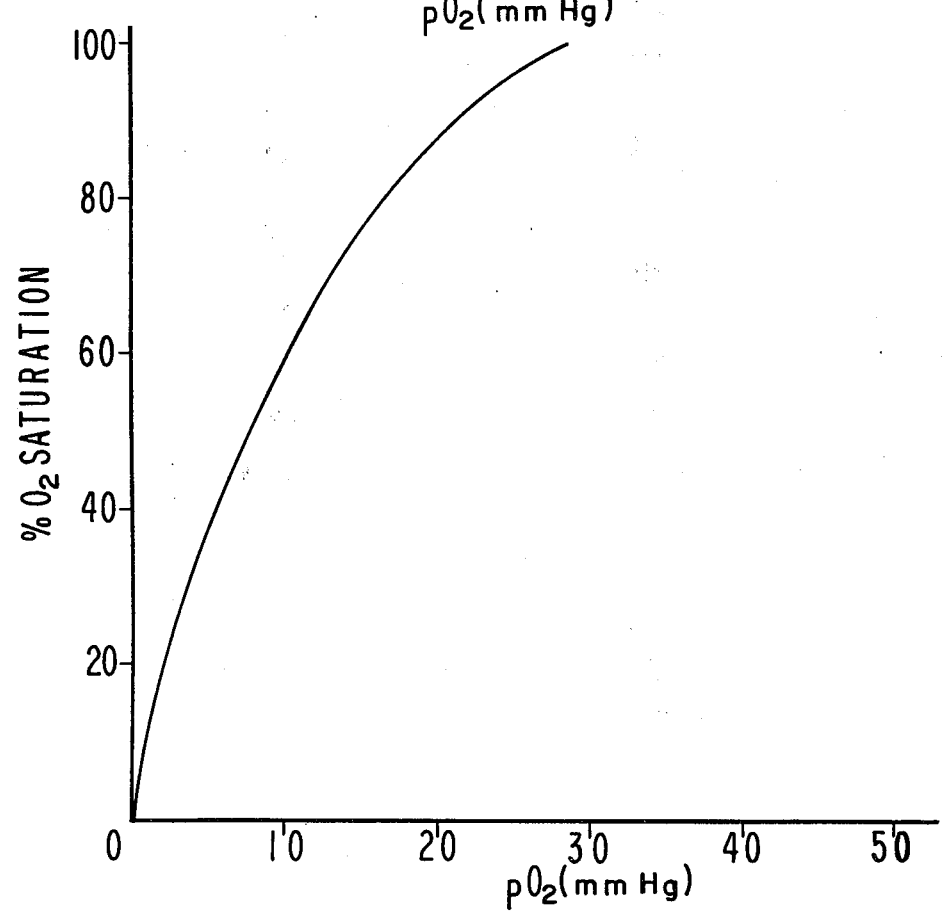

Intramolecular cross-linking of stromal-free oxyhemoglobin with hexamethylene diisocyanate. The procedures of Examples I and II were followed in this procedure and all conditions were as described except that conformational state of the hemoglobin tetrameric molecule was in the high affinity oxy form, and the intramolecular cross-linking was carried out in a 100% air atmosphere. In accompanying FIG. 2, the oxygen dissociation curve for intramolecularly cross-linked, stromal-free oxyhemoglobin prepared according to this example is set forth. The product shows a $P_{50}$ value of 8 mm Hg at 37° C and neutral pH.

EXAMPLE IV

Figure 3:
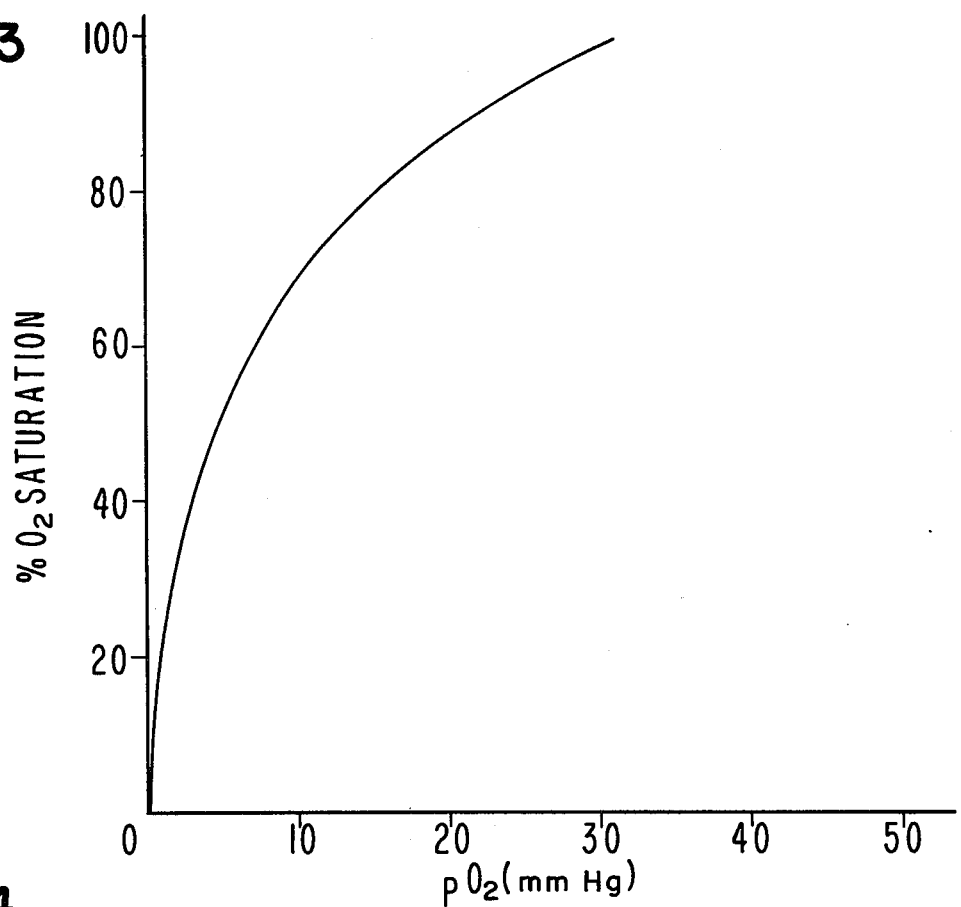

Preparation of intramolecularly cross-linked stromal-free oxyhemoglobin with butadiene diepoxide. Butadiene diepoxide, 577 mg, was added to 45 ml of stromal-free oxyhemoglobin, 12% w/v in 0.05 M borate buffer, pH 8.9. The solution was left stirring at 4° C under air for 2 days to yield intramolecularly cross-linked, stromal-free oxyhemoglobin having a molecular weight of about 64,500. In accompanying FIG. 3, the oxygen dissociation curve for intramolecularly cross-linked, stromal-free oxyhemoglobin is set forth. The product has a $P_{50}$ of 4.5 mm Hg at 37° C and neutral pH.

EXAMPLE V

Figure 4:
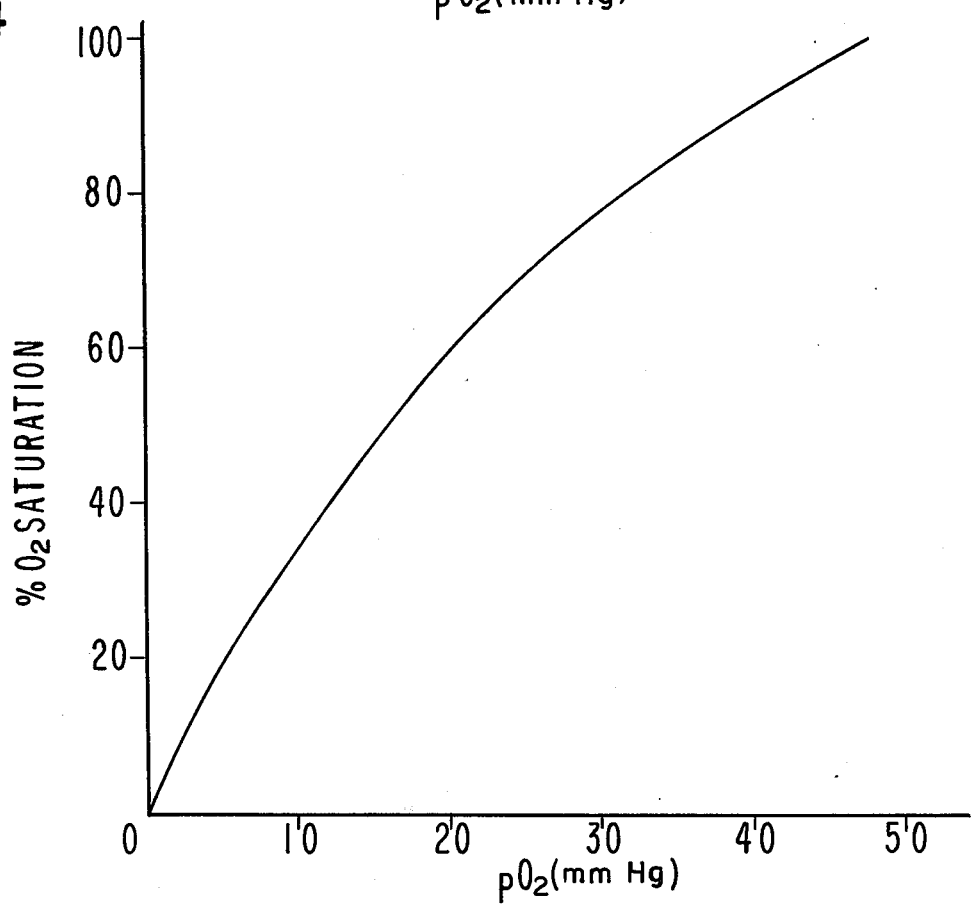

Preparation of intramolecularly cross-linked stromal-free deoxyhemoglobin with butadiene diepoxide. To 13 ml of stromal-free deoxyhemoglobin prepared according to Examples 1 and 2, as 12.5% w/v in 0.05 M phosphate buffer, pH 6.9, was added 42 mg of butadiene diepoxide as a neat reagent. The reaction was left stirring at 4° C under a constant flow of moist nitrogen gas for 144 hours. Next, the sample was oxygenated, the pH adjusted to 8.0 with 1 N NaOH, and treated with 140 mg of 2-aminoethane thiol hydrochloride in 1 ml of 0.05 M phosphate buffer, pH 7.6. The reaction was left stirring at 4° C overnight to yield the product. In accompanying FIG. 4 the oxygen dissociation curve for intramolecularly cross-linked, stromal-free deoxyhemoglobin prepared according to this example is set forth. The product has a $P_{50}$ of 16 mm Hg at 37° C and neutral pH.

EXAMPLE VI

Figure 5:
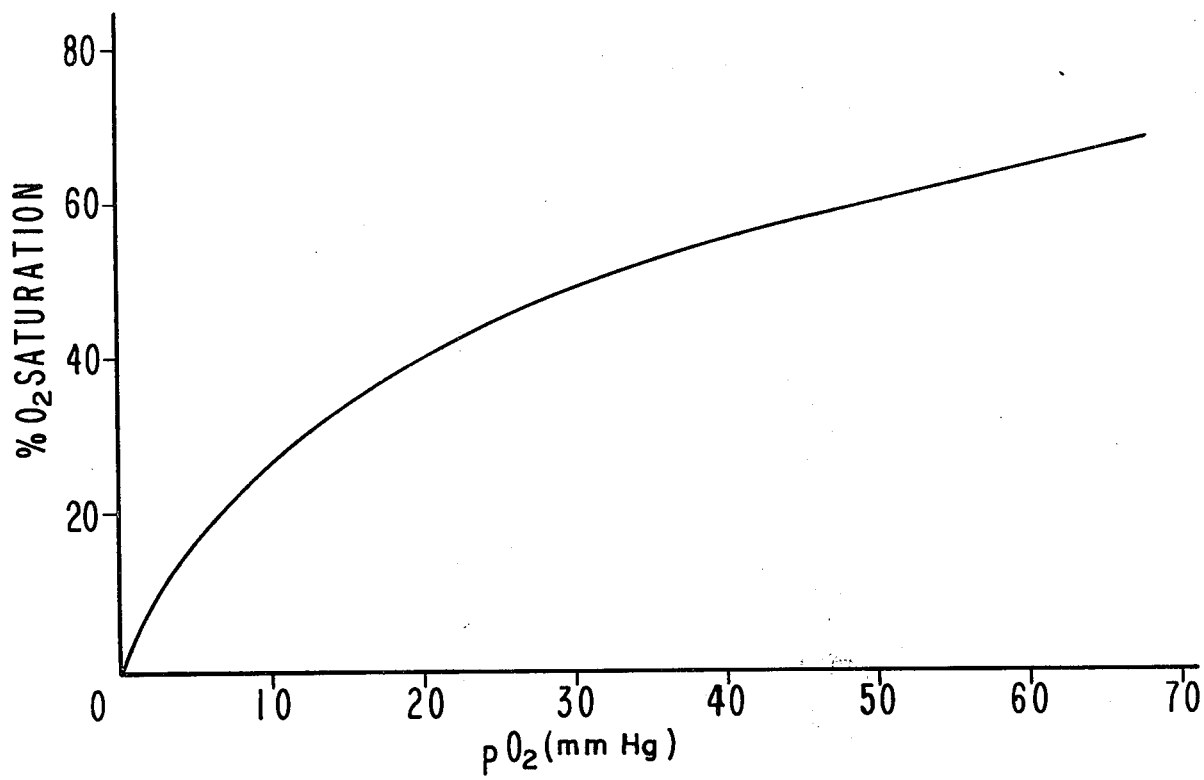

Preparation of intramolecularly cross-linked stromal-free deoxyhemoglobin with divinyl sulfone. To 40 ml of deoxyhemoglobin, 9% w/v, in 0.05 M phosphate buffer at pH 7.4, was added 0.11 ml of divinyl sulfone as a neat liquid. The reaction was left stirring at 4° C under a constant flow of nitrogen for four hours, at which time 3 ml of 1.3 M L-lysine in 0.05 M phosphate buffer, pH 7.2, was added to quench the reaction. The reaction was stirred at 4° C overnight in an inert atmosphere substantially free of air and oxygen to yield intramolecularly cross-linked, stromal-free deoxyhemoglobin having a molecular weight of approximately 64,500. In accompanying FIG. 5 the oxygen dissociation curve for intramolecularly cross-linked, stromal-free deoxyhemoglobin prepared according to this example is set forth. The product has a $P_{50}$ of 31 mm Hg at 37° C and neutral pH.

EXAMPLE VII

Figure 6:
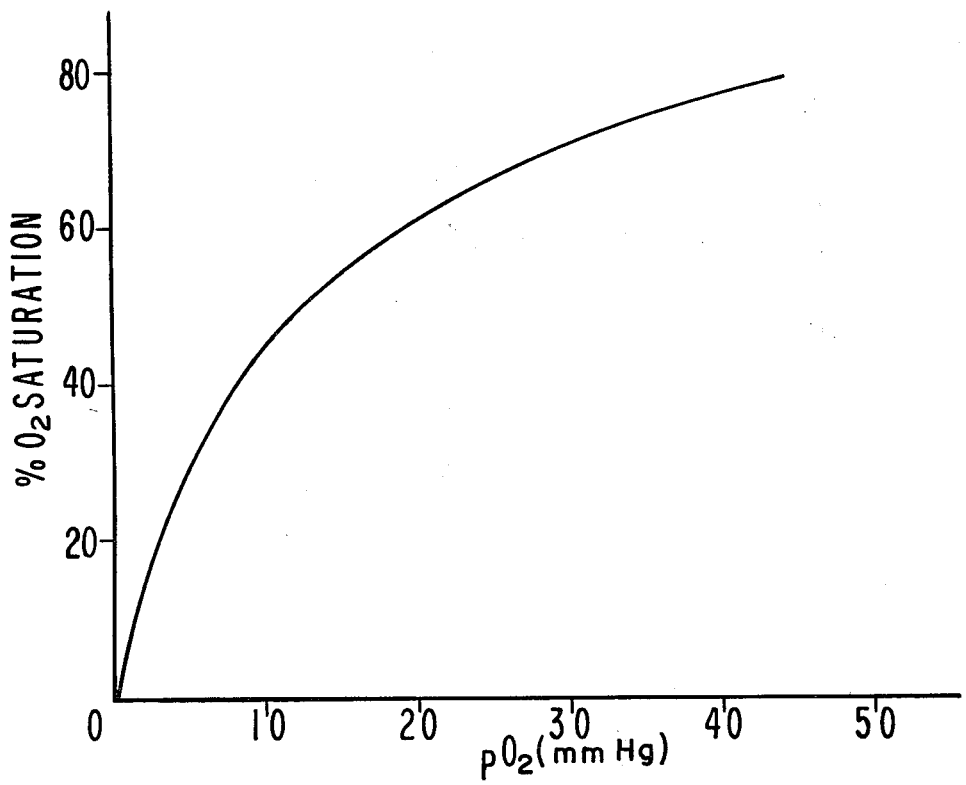

Reaction of oxyhemoglobin with divinyl sulfone. To 40 ml of oxyhemoglobin, 9% w/v, in 0.05 M phosphate buffer at pH 7.4, was added with stirring 0.044 ml divinyl sulfone as a neat liquid. Then, the reaction was continuously stirred at 4° C in air for 84 hours, at which time the reaction was quenched by the addition of 3 ml of 1.3 M L-lysine in 0.05 M phosphate buffer, pH 7.2. The reaction was stirred an additional 24 hours to yield intramolecularly cross-linked, stromal-free oxyhemoglobin having a molecular weight of approximately 64,500. In accompanying FIG. 6 the oxygen dissociation curve for intramolecularly cross-linked, stromal-free, oxyhemoglobin prepared according to this example is set forth. The product has a $P_{50}$ of 12.5 mm Hg at 37° C and neutral pH.

EXAMPLE VIII

Figure 7:
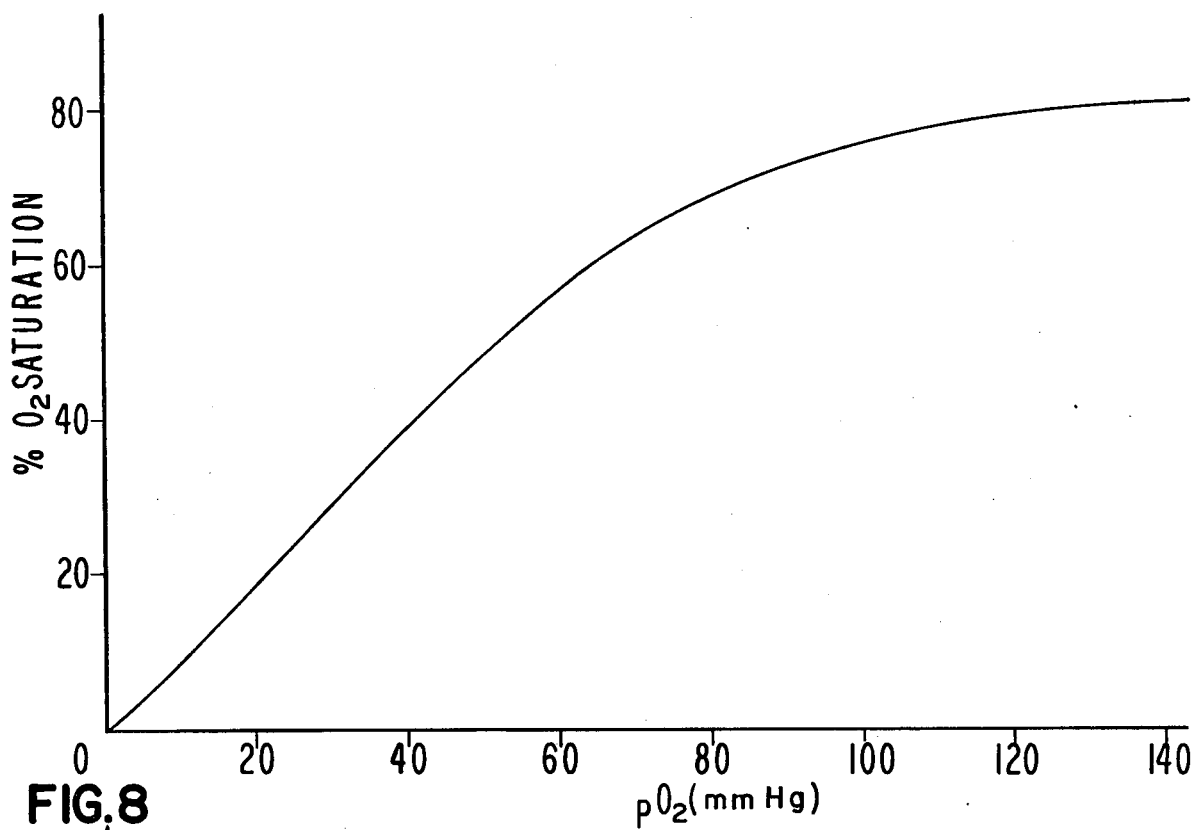

Reaction of deoxyhemoglobin with divinyl sulfone. To 22 ml of freshly prepared stromal-free deoxyhemoglobin, 10.3% w/v in 0.05 M phosphate buffer, pH 7.9, was added 0.025 ml of divinyl sulfone as a neat liquid. Next, the reactants were stirred at 4° C under a continuous flow of moist nitrogen for 72 hours, followed by quenching by adding 3 ml of deoxygenated 1.3 M of L-lysine in 0.05 M phosphate buffer, pH 7.2. The reaction solution was left standing at 4° C under a nitrogen atmosphere an additional 24 hours to yield intramolecularly cross-linked stromal-free deoxyhemoglobin. In accompanying FIG. 7 the dissociation curve for intramolecularly cross-linked, stromal-free deoxyhemoglobin prepared according to this example is set forth. The product has a $P_{50}$ of 52 mm Hg at 37° C and neutral pH.

EXAMPLE IX

Figure 8:
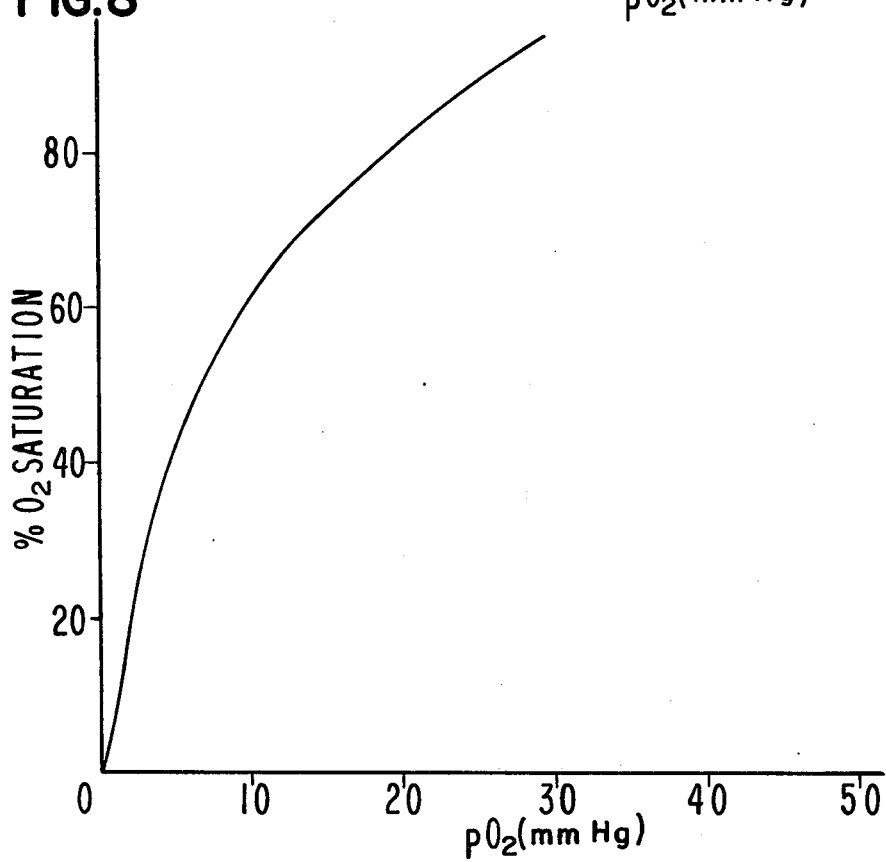

Reaction of oxyhemoglobin with divinyl sulfone. Stromal-free oxyhemoglobin was intramolecularly cross-linked with divinyl sulfone according to the procedure described in Example VI, with all conditions as described except that the reaction was carried out in an air environment and the hemoglobin was stromal-free oxyhemoglobin. In accompanying FIG. 8 the oxygen dissociation curve for intramolecularly cross-linked, stromal-free oxyhemoglobin prepared according to Example IX is set forth. The product has a $P_{50}$ of 7 mm Hg at 37° C at neutral pH.

The reaction solutions prepared according to Example II through IX were purified as follows: first, the reaction solutions were centrifuged for 20 minutes at 40,000g. The purification steps, and all previous steps were carried out at temperatures of less than 10° C to minimize any possible oxidation of the intramolecularly cross-linked, stromal-free deoxyhemoglobin and oxyhemoglobin. Next, the solutions were filtered through a filter having a pore size of 0.6 μm, and dialyzed against an excess of normal saline. These steps insure removal of insoluble denatured protein and excess reagents used during the cross-linking reactions. The pH of the purified solutions were adjusted to the desired pH by dropwise addition of 0.1 N HCl or 1 N NaOH. Finally, the solutions were centrifuged again, for 20 minutes at 40,000g, and sterilized by filtration through a filter having a pore size of 0.2 μm. The above procedures are disclosed and described in detail with references in U.S. patent application Ser. Nos. 553,514 filed on Feb. 2, 1975 and 554,051 filed on Feb. 2, 1975. The disclosures of these applications are incorporated herein by reference.

DESCRIPTION OF APPLICATION OF THE INVENTION

The intramolecularly cross-linked, stromal-free deoxyhemoglobin and intramolecularly cross-linked, stromal-free oxyhemoglobin prepared according to the invention have a reversible ligand binding property. That is, these intramolecularly cross-linked biologically acceptable hemoglobins possess the ability to become saturated with a ligand such as oxygen, and to transport and release it to an environment of use or to a ligand receptor. This property makes the products of this invention useful as a blood substitute. The intramolecularly cross-linked, stromal-free products are soluble in aqueous media, blood, plasma, crystalloid, buffered electrolyte, colloid, carbohydrate and polymeric solutions. The products have a physiologically acceptable colloidal-osmotic properties and uniform molecular weights which make them useful as a blood plasma expander. The intramolecularly cross-linked, stromal-free deoxyhemoglobin and oxyhemoglobin prepared according to Examples II to IX have an increased plasma residence time greater than noncross-linked hemoglobin. The products of this invention exhibited in laboratory male rats an increased in vivo half life, $T_{\frac{1}{2}} >$ 180 minutes, compared to noncross-linked hemoglobin which exhibited a $T_{\frac{1}{2}} <$ 90 minutes. Additionally, since the intramolecularly cross-linked products are stromal-free, deleterious effects on the renal system are prevented. In this application, the term "substantially stromal-free" means the products do not contain any red cell stromal material, including phospholipids and lipids, and the terms "half-life" and "$T_{\frac{1}{2}}$" mean the period in which the initial amount of the product in an in vivo environment falls to half its initial value.

The intramolecularly cross-linked, stromal-free deoxyhemoglobin and the intramolecularly cross-linked, stromal-free oxyhemoglobin can be used as a blood substitute, and blood plasma expander alone or mixed with a pharmaceutically acceptable carrier, or with other plasma substitutes or blood plasma expanders. The carriers can be crystalloids including physiological saline, a mixture consisting of saline and glucose, Ringer's solution, lactated Ringer's solution, Locke-Ringer's solution, Krebs-Ringer's solution, Hartmann's balanced saline, and heparinized sodium citrate-citric acid-dextrose solution.

The intramolecularly cross-linked, stromal-free deoxyhemoglobin and oxyhemoglobin can be mixed with water soluble physiologically acceptable polymeric plasma substitutes such as poly(ethylene oxide), poly(acrylamide), poly(vinyl pyrrolidone), poly(vinyl alcohol), and ethylene oxide-poly(propylene glycol) condensates. Additionally, the hemoglobins can be mixed with colloidal-like plasma substitutes and blood plasma expanders such as linear polysaccharides including dextrans having a molecular weight of 40,000 to 70,000, gum arabic, pectins, balanced fluid gelatin, and hydroxyethyl starch. Generally, for the purpose of the invention, the intramolecularly cross-linked, stromal-free deoxyhemoglobin and oxyhemoglobin is contained in a composition comprising about 1to 10 percent admixed with one of the above carriers or with a mixture thereof. The compositions are prepared by blending the respective ingredients in a predetermined proportion to produce compositions. For example, a blood substitute solution comprising 5% intramolecularly cross-linked, stromal-free deoxyhemoglobin or oxyhemoglobin in normal saline is prepared by adding 5 grams of said hemoglobin to physiological saline, which is 0.85% sodium chloride in water, with q.s. to 100 ml. These compositions are administered in the manner commonly employed in the blood transfustion art as disclosed in *Practical Blood Transfusion,* by Hustis, Bove and Busch, 1969, published by Little, Brown and Company, Boston.

Other applications for the hemoglobins of the invention include their use as artificial oxygen exchange solutions in conventional oxygenators, such as cardiac by-pass extracorporeal circulatory assist devices, hollow fiber and sheet-type membrane devices, as used for assisting circulation in ill patients. For these conditions, oxygenators are widely used to mechanically oxygenate venous blood extracorporeally. In operation, an oxygenator has one or more pumps for maintaining circulation and for perfusion of oxygen by the exchange of gases between blood in an isolated vascular bed and oxygen across an oxygenation membrane.

An oxygen exchange membrane is prepared according to the invention by saturating a porous synthetic semipermeable membrane, such as cellophane or a Millipore ® filter having a pore size of 0.45, 0.30 or 0.22 microns, a porosity of 75% and a thickness of 150 mm by soaking the membrane in an aqueous solution of the hemoglobin of the invention to immobilize it within the micropores. The saturated membrane is next mounted in an oxygenator, attached to a source of oxygen having a gas flow meter to control the volumeric rate of oxygen delivered by the hemoglobin oxygenation membrane to blood in the vascular system.

The intramolecularly cross-linked, stromal-free deoxyhemoglobin and oxyhemoglobin can be used as a source of protein and oxygen in the microbiological assay of foods for aerobic bacillus and staphylococus to insure the food is safe for animal and human consumption. The hemoglobins can be used for the storage and preservation of viable isolated perfused mammalian organs for their eventual transplant into a recipient, as a substitute for the oxygen-carrying capacity of red cells in mammals, and the hemoglobins can be used to supply oxygen as an aid in uranium leaching as disclosed in U.S. Pat. No. 3,003,848, and as a scavenger of noxious gases such as carbon monoxide and nitrogen oxide, and as a means for the purification of oxygen.

In summary, it will be appreciated by those versed in the art that it has now been found that both intramolecularly cross-linked, stromal-free deoxyhemoglobin and intramolecularly cross-linked stromal-free oxyhemoglobin can be prepared according to the mode and manner of this invention; and that they are endowed with the similar beneficial properties of macromolecular cross-linked, stromal-free hemoglobin disclosed in applicants' copending application Ser. Nos. 553,514 and 554,051. For example, intramolecularly and intermolecularly cross-linked stromal-free hemoglobins will have the following therapeutic benefits for treating circulatory shock, compared to the corresponding use of noncross-linked hemoglobin: (a) an increased half-life dependent on the molecular weight of the cross-linked stromal-free hemoglobin, (b) variable oxygen affinities dependent on the method of preparing the product, and (c) increased chemical stability.

Additionally, the cross-linked hemoglobins can be made iso-osmotic by the addition of pharmaceutically acceptable electrolytes, mainly sodium chloride. The oncotic pressure exerted in vivo by each of the these is a function of molecular weight, since oncotic pressure is a colligative property directly dependent on the number of macromolecules in a given solution. For instance, albumin which has a molecular weight of about 69,000 normally supplies the required in vivo pressure to prevent circulatory collapse. In conditions where there is a loss of blood, there is an accompanying loss of albumin, which is usually treated by intravenously administering a plasma expander. Thus, the treatment of blood loss is two-fold, (a) replacement of fluid and (b) replacement of oxygen carriers. Both intramolecularly cross-linked stroma-free oxyhemoglobin and deoxyhemoglobin and intermolecularly cross-linked stroma-free oxyhemoglobin and deoxyhemoglobin are effective replacements for blood loss, and properties exhibited by these beneficial products make available a broader choice of blood replacement therapy than previously known. For example, macromolecular, intermolecularly cross-linked stromal-free hemoglobin might be the preferred therapeutic agent during those surgical procedures and replacement therapies where a long in vivo plasma half-life is desired. The less pronounced oncotic activity exhibited by such macromolecular hemoglobin is simply accomodated by addition of the traditional plasma expanders, for example dextron or albumin. In such cases polyhemoglobins serve primarily as long-lived oxygen carriers. Under other circumstances, the preferred therapeutic method of treating blood loss might require a combination of both enhanced oncotic activity and oxygen delivery and in these cases the intramolecularly cross-linked stromal-free hemoglobins having a molecular weight equal to albumin might be the indicated therapeutic agent, even though the half-life of these materials are less than those of intermolecularly cross-linked hemoglobin. The final choice allowed the practioner of blood replacement therapy is that of oxygen binding functionality. Each polyhemoglobin exhibits unique binding functionality which is reflected in the $P_{50}$ value, determined from the oxygen dissociation curve. Presently, such a choice is not available to practioners of blood replacement therapy. The therapeutic advantages of blood replacement with polyhemoglobins lies mainly in the versatility of their physical properties, and intramolecularly cross-linked stromal-free polyhemoglobins adds to this versatility.

It will be further appreciated that this invention provides products that are reliable means for transporting and supplying the ligand oxygen to vital tissues and organs in animals including domestic animals such as dogs and cats, farm animals such as cows and pigs, and to mammals including warm-blooded mammals without obtaining unwanted effects. And, while the invention has been described with reference to certain presently preferred embodiments thereof, those skilled in the art will appreciate that various modifications, changes, omissions and substitutions can be made without departing from the spirit of the invention.

We claim:

1. A pharmaceutical composition useful as a blood substitute and blood plasma expander comprising a therapeutically effective amount of intramolecularly cross-linked, stromal-free deoxyhemoglobin, soluble in aqueous and physiological fluids, capable of reversibly binding a ligand, having a molecular weight of about 64,500, and mixed with a pharmaceutically acceptable carrier.

2. The pharmaceutical composition according to claim 1 wherein the intramolecularly cross-linked, stromal-free deoxyhemoglobin is soluble in aqueous and pharmaceutically acceptable liquid carriers.

3. The pharmaceutical composition according to claim 1 wherein the pharmaceutically acceptable carrier is a member selected from the group consisting of crystalloid, colloidal, polymeric, carbohydrate solutions, and mixtures thereof.

4. The pharmaceutical composition according to claim 1 wherein the carrier is a liquid, containing from 2 to 15% of the intramolecularly cross-linked, stromal-free deoxyhemoglobin with said deoxyhemoglobin having a partial oxygen pressure at half-saturation, $P_{50}$, between 4 mm Hg and 100 mm Hg at physiological temperature and pH.

5. The pharmaceutical composition according to claim 1 wherein the intramolecularly, cross-linked, stromal-free deoxyhemoglobin has oxygen transport capacity and reversible oxygen binding capacity when mixed with the carrier, with said deoxyhemoglobin formed by cross-linking 1 mole deoxyhemoglobin tetramer with 1 to 50 moles of a cross-linking agent.

6. The pharmaceutical composition according to claim 1 wherein the pharmaceutically acceptable carrier is a crystalloid selected from the group consisting of saline, a mixture of saline and glucose, and sodium-citric acid-dextrose solution.

7. The pharmaceutical composition according to claim 1 wherein the pharmaceutically acceptable carrier is a member selected from the group consisting of poly(ethylene oxide), poly(acrylamide), poly(vinyl pyrrolidone), poly(vinyl alcohol), and ethylene oxide-poly(propylene glycol)condensates.

8. The pharmaceutical composition according to claim 1 wherein the pharmaceutical acceptical carrier is a member selected from the group consisting of poly(saccharides), dextran, gum arabic, plasma protein, albumin, pectin, fluid gelatin, and hydroxyethyl starch.

9. A method for increasing the volume of the blood circulatory system wherein the method comprises transfusing into the system of a warm blooded animal having a decreased blood volume, a quantity of blood volume expander comprising intramolecularly cross-linked, stromal-free deoxyhemoglobin having a molecular weight of about 64,500 and an increased residence time at least two times greater than noncross-linked hemoglobin.

10. A method for the treatment of shock which method comprises administering into the circulatory system of an aminal in shock, a blood plasma substitute comprising intramolecularly cross-linked, stromal-free dexoyhemoglobin having a molecular weight of about 64,500 in an isotonic, physiologically acceptable solution, and in an effective amount to alleviate said shock.

11. A method for supplying oxygen (a) to animal tissues and organs, and (b) for maintaining isolated animal organs in a viable state, which method comprises (c) transfusing an effective amount of intramolecularly cross-linked, stromal-free deoxyhemoglobin into the circulatory system of an animal for supplying oxygen to said tissues and organs (d) perfusing the isolated organ with an effective amount of a perfusate comprising intramolecularly cross-linked, stromal-free deoxyhemoglobin, and wherein the deoxyhemoglobin transfused and perfused in (c) and (d) has a molecular weight of about 64,500 and is mixed with a pharmaceutically acceptable carrier.

12. A method for increasing the shelf-life and in vivo life of hemoglobin which method comprises the steps of separating erythrocyctes from blood, lysing the erythrocytes to disrupt the cellular wall of the erythrocytes, isolating hemoglobin from the lysed erythrocytes substantially-free of cellular wall material and stroma, converting the isolated hemoglobin to deoxyhemoglobin, intramolecularly cross-linking the stromal-free deoxyhemoglobin with a polyfunctional, covalent cross-linking agent to form intramolecularly, cross-linked, stromal-free deoxyhemoglobin, soluble in aqueous and physiological fluids, capable of reversibly binding, a ligand, having a molecular weight of 64,500, and wherein said intramolecularly cross-linked, stromal-free deoxyhemoglobin has an increased shelf-life, an increased in vivo persistance in an animal at least twice that of noncross-linked hemoglobin.

13. Intramolecularly, cross-linked, stromal-free deoxyhemoglobin, having an increased intravascular persistance, a molecular weight of about 64,500, soluble in aqueous and physiological fluids, capable of transporting and reversibly binding a ligand, and a partial oxygen pressure at half-saturation, $P_{50}$, of at least 4 mm Hg at physiological temperature and physiological pH.

14. A pharmaceutical composition useful as a blood substitute and blood plasma expander comprising a therapeutically effective amount of intramolecularly, cross-linked, stromal-free oxyhemoglobin formed by cross-linking at least 1 mole oxyhemoglobin tetramer with at least 1 mole of a covalent, cross-linking agent selected from the group consisting of heterocyclic triazines, bis(diazobenzidines, halogenated aromatic cycloalkanes having at least two cross-linking moieties, dialdehydes, glutaraldehyde, divinyl sulfone, diisoyanates, and diepoxides, and wherein said hemoglobin is soluble in aqueous and physiological fluids, capable of reversibly binding with a ligand, and has a molecular weight of about 64,500, and is mixed with a pharmaceutically acceptal carrier.

15. The pharmaceutical composition according to claim 14 wherein the pharmaceutical acceptable carrier is a member selected from the group consisting of crystalloid colloidal, polymeric, and poly(saccharide) carriers, and mixtures thereof.

16. The pharmaceutical composition according to claim 14 wherein the intramolecularly cross-linked, stromal-free oxyhemoglobin is soluble in aqueous and pharmaceutically acceptable liquid carriers, and wherein the composition contains from 2 to 15% of the oxyhemoglobin with said oxyhemoglobin having a partial oxygen pressure at half-saturation, $P_{50}$, between 2.5 mm Hg and 25 mm Hg at physiological temperature and pH.

17. The pharmaceutical composition according to claim 14 wherein the carrier is (a) a crystalloid selected from the group consisting of saline, a mixture of saline and glucose, and sodium citrate-citric acid-dextrose solution (b) a polymeric carrier selected from the group consisting of poly(ethylene oxide), poly(acrylamide, poly(vinyl pyrrolidone), poly(vinyl alcohol), ethylene oxide-poly(propylene glycol) condensates, and (c) a member selected from the group consisting of dextran, poly(saccharides), gum arabic, pectin, fluid gelatin, hydroxyethyl starch, plasma protein, and albumin.

18. A method for increasing the volume of the blood circulatory system, comprising transfusing into the system of a warm blooded animal having a decreased volume, a quantity of blood volume expander comprising intramolecularly cross-linked, stromal-free oxyhemoglobin, having a molecular weight of about 64,500, an increased residence time greater than noncross-linked oxyhemoglobin, and cross-linked with a convalent cross-linking agent selected from the group consisting of heterocyclic triazines, bis(diazobenzidines), halogenated aromatics, cycloalkanes having at least two cross-linking moieties, dialdehydes, glutareldehyde, divinyl sulfone, diisocyanates and diepoxides, and wherein the quantity transfused is an effective amount for increasing the volume of the system.

19. A method for the treatment of shock which method comprises administering into the circulatory system of an animal in shock, a blood plasma substitute comprising intramolecularly cross-linked, stromal-free oxyhemoglobin, having a molecular weight of about 64,500, cross-linked with a covalent cross-linking agent selected from the group consisting of heterocyclic triazines, bis(diazobenzidines), halogenated aromatic, cycloalkanes having at least two cross-linking moieties, dialdehydes, glutaraldehyde, divinyl sulfone, diisocyanates, and diepoxides, and wherein the hemoglobin is mixed with an isotonic physiologically acceptable carrier and is administered in an effective amount for alleviating said shock.

20. A method for supplying oxygen (a) to animal tissues and organs, and (b) for maintaining isolated animal organs in a viable state, which method comprises, (c) transfusing an effective amount of intramolecularly cross-linked stromal-free oxyhemoglobin into the circulatory system of an animal for supplying oxygen to said tissues and organs, (d) perfusing the isolated organ with an effective amount of a perfusate comprising intramolecularly cross-linked stromal-free oxyhemoglobin, and wherein the oxyhemoglobin has a molecular weight of about 64,500 and is mixed with a pharmaceutically acceptable, liquid carrier.

21. A method for increasing the shelf-life and in vivo life of oxyhemoglobin which method comprises the steps of separating erythrocytes from whole blood, lysing the erythrocytes to disrupt the cellular wall of the erythrocytes, isolating oxyhemoglobin from the lysed erythrocytes substantially free of cellular wall material and stroma, cross-linking the stromal-free oxyhemoglobin with a polyfunctional, covalent, cross-linking agent in an oxygen containing environment to form intramolecularly cross-linked, stromal-free oxyhemoglobin, soluble in aqueous and physiological fluids, capable of binding oxygen and releasing it in vivo, having a molecular weight of 64,500, and wherein said intramolecularly cross-linked, stromal-free oxyhemoglobin has an increased shelf-life an increased in vivo peristence in an animal at least twice that of noncross-linked oxyhemoglobin, and has an osmolarity substantially equal to whole blood.

22. Intramolecularly cross-linked, stromal-free oxyhemoglobin formed by cross-linking oxyhemoglobin with a covalent cross-linking agent selected from the group consisting of heterocyclic triazines, halogenated aromatic cycloalkanes having at least two cross-linking sites, dialdehydes, glutaraldehyde, divinyl sulfone, diisocyanates and diepoxides, said oxyhemoglobin having an increased intravascular peristance, a molecular weight of about 64,500, soluble in aqueous and physiological fluids, capable of reversibly binding a gaseous ligand, and having a partial oxygen pressure at half-saturation, $P_{50}$, of at least 2.5 mm Hg at physiological temperature and physiological pH.

* * * * *